United States Patent
Farrugia et al.

(10) Patent No.: US 8,353,289 B2
(45) Date of Patent: Jan. 15, 2013

(54) USING MOTOR SPEED IN A PAP DEVICE TO ESTIMATE FLOW

(75) Inventors: Steven Paul Farrugia, Lugarno (AU); Kristian Thomsen, Calamvale (AU); Matthew Alder, Scarborough (AU); Tracey Bullivant, North Ryde (AU)

(73) Assignee: ResMed Limited (AU)

( * ) Notice: Subject to any disclaimer, the term of this patent is extended or adjusted under 35 U.S.C. 154(b) by 963 days.

(21) Appl. No.: 12/294,957

(22) PCT Filed: Nov. 2, 2005

(86) PCT No.: PCT/AU2005/001688
§ 371 (c)(1),
(2), (4) Date: Oct. 30, 2008

(87) PCT Pub. No.: WO2006/047826
PCT Pub. Date: May 11, 2006

(65) Prior Publication Data
US 2010/0319697 A1 Dec. 23, 2010

Related U.S. Application Data

(60) Provisional application No. 60/624,951, filed on Nov. 4, 2004, provisional application No. 60/625,878, filed on Nov. 8, 2004.

(51) Int. Cl.
*A61M 16/00* (2006.01)
*A62B 7/00* (2006.01)

(52) U.S. Cl. ......... 128/204.18; 128/200.24; 128/204.21; 417/44.1

(58) Field of Classification Search ............. 128/200.24, 128/204.18, 204.21; 417/44.1
See application file for complete search history.

(56) References Cited

U.S. PATENT DOCUMENTS

| | | | |
|---|---|---|---|
| 5,443,061 A | 8/1995 | Champlain et al. | |
| 5,671,730 A | 9/1997 | Ollila | |
| 5,740,795 A | 4/1998 | Brydon | |
| 6,237,593 B1 | 5/2001 | Brydon | |
| 6,283,119 B1 | 9/2001 | Bourdon | |
| 6,353,302 B1 * | 3/2002 | Ramachandran et al. | 318/727 |
| 6,998,812 B2 * | 2/2006 | Kerner et al. | 318/648 |

(Continued)

FOREIGN PATENT DOCUMENTS

EP 1393767 3/2004

(Continued)

OTHER PUBLICATIONS

Notice of Reasons for Rejection, Japan Patent Application No. P2007-538221l, Japanese Patent Office, Jan. 25, 2011.

*Primary Examiner* — Lynne Anderson
*Assistant Examiner* — Bradley Philips
(74) *Attorney, Agent, or Firm* — Lerner, David, Littenberg, Krumholz & Mentlik, LLP

(57) ABSTRACT

A method and apparatus are disclosed for determining airflow through a PAP device while applying PAP therapy. The actual speed of a blower 6 is measured. The desired motor current IDES required for the actual speed to approach or maintain a desired speed is used, together with the actual speed RPM ACT, in a flow estimation algorithm to determine flow through the PAP device. The estimation algorithm consists of a two-dimensional look-up table, where the inputs are the desired motor current and actual motor speed, and the output is the flow through the PAP device.

15 Claims, 4 Drawing Sheets

U.S. PATENT DOCUMENTS 7,077,131 B2 * 7/2006 Hansen .................... 128/204.18
2005/0268913 A1 * 12/2005 Morris et al. ............ 128/204.23

FOREIGN PATENT DOCUMENTS

| JP | 2002-098088 | 11/2007 |
| WO | 97/10019 | 3/1997 |
| WO | 02/23298 | 3/2002 |
| WO | WO 0223298 A1 * | 3/2002 |
| WO | 02/26305 | 4/2002 |
| WO | 2005/87319 | 9/2005 |

* cited by examiner

USING MOTOR SPEED IN A PAP DEVICE TO ESTIMATE FLOW

RELATED APPLICATIONS

This application claims the priority of U.S. provisional application Ser. No. 60/624,951 filed on Nov. 4, 2004 and U.S. provisional application Ser. No. 60/625,878 filed on Nov. 8, 2004.

FIELD OF THE INVENTION

The present invention relates to the estimation of flow in a positive airway pressure (PAP) device without the use of sensors.

BACKGROUND OF THE INVENTION

A Positive Airway Pressure (PAP) device is used in the treatment of sleep related breathing disorders such as Obstructive Sleep Apnea (OSA). A typical device consists of a flow generator which delivers pressurized air to a patient via an air delivery hose connected to a face mask. At its simplest level, the flow generator consists of a blower that can deliver a prescribed pressure (up to 30 cmH$_2$O) to the patient, as set by a clinician.

High end PAP devices claim to be more effective in the treatment of OSA because they can monitor the air flow delivered to the patient and derive a measure of the effectiveness of the treatment pressure. Using this information, the quality of treatment can be improved and reported back to a clinician for review. In an auto-titrating device (APAP), the delivered pressure can be continually adjusted to the minimum required pressure for effective treatment.

Traditional techniques used to measure flow in a PAP device involve inserting a flow sensor in the air path. The sensor may be of a Venturi type, which measures a pressure drop across a section of the air path, usually across some known pneumatic resistance. Another sensing technique is the thermal mass flow sensor, which allows the air to pass over a heated element with the temperature being measured downstream of the element. These techniques are accurate yet add extra costs to the PAP device due to the sensing hardware.

Several patents have been granted on devices for treating disordered breathing that are capable of operation with traditional flow sensors. Once example is U.S. Pat. No. 5,443,061 to Champain, et al., titled "Apparatus for providing a breathing gas with an overpressure and process of controlling such apparatus installation." Champain uses a piezoelectric pressure sensor for detecting airflow fluctuations between a turbine and a mask. The output of the sensor is provided to a turbine controller, which adjusts the turbine accordingly.

Other examples of relevant prior patents include U.S. Pat. Nos. 5,740,795 and 6,237,593, both to Brydon, both having the same assignee as the present invention and both teaching "Estimation of flow and detection of breathing in CPAP treatment" (collectively "Brydon"). Brydon states that the speed of a blower motor is controlled by a feedback loop in which actual motor speed is measured and an error signal is generated to increase or decrease drive to the motor or other regulating device, thus maintaining a constant motor speed ('795 patent, col. 2, lines. 55-65). The structure for performing the speed control includes a motor controller which issues a control signal to control the motor speed. A speed feedback signal is inputted into the motor controller which provides the signal upon which speed regulation is based.

Brydon also states that signals can be derived from motor speed and power measurements and bear a non-linear relationship to the actual volumetric flow. These signals may be linearized using empirically determined pressure/flow/speed characteristics of the turbine system to give a volumetric measure of patient respiration (flow) (795 patent, col. 3, lines. 5-15). Regarding power measurements, Brydon states that current alone is typically a sufficient indicator of motor power. To measure current, Bydon teaches a current sensing resistor and measurements of the voltage drop across the resistor. The voltage is sensed and provided to a differential amplifier, whose output is a signal representative of motor current (and power). The signal is then provided to a low-pass filter circuit that removes high frequency electrical noise, providing the average or steady state component of the signal. The signal is then extended through a high-pass filter to remove non-respiratory components and then applied to a single-dimension linearization element, the function of which is derived from empirically determined pressure/flow/speed characteristics of the turbine, tube and mask system. The output of the linearization element is a linearized flow signal.

The problem with the Brydon approach is that motor current is very noisy. In FIG. 1, the top-trace 2 is mask pressure, while the bottom trace 4 is the motor current. For a large pressure step, the current trace indicates significant noise because of the summation of switching currents through motor drive MOSFETs that are usually used. It can be appreciated that for small pressure or flow perturbations, the signal noise becomes even more significant.

The flow information read from auto-titrating (APAP) and high-end constant pressure (CPAP) PAP devices does not necessarily require the accuracy provided by hardware flow sensors. Therefore, a flow estimator would provide an alternative, low-cost method to provide flow data, usable where cost requirements prohibit the use of sensors.

OBJECTS AND SUMMARY OF THE INVENTION

It is an object of the invention to develop an improved algorithmic flow estimator for use in a PAP device in place of traditional flow measurement sensors. An algorithmic flow estimator would have the advantage of low cost compared with a physical sensor and the associated electronics. An algorithmic flow estimator would not introduce pressure loss to the air delivery circuit, unlike physical sensors which typically have a high insertion loss.

To satisfy the recited objectives, a method and apparatus are disclosed for determining airflow through a PAP device while applying PAP therapy. The method comprises the steps of generating a parameter having a speed dimension that is based on the actual speed of a blower motor, generating a parameter having a current dimension that is based on operating characteristics of said blower motor, and using the speed-dimension parameter and the current-dimension parameter in a flow estimation algorithm to determine flow through the PAP device. The preferred embodiment of the invention comprises the steps of measuring the actual speed of the blower motor, determining the desired motor current for achieving the desired motor speed, and using both the actual blower motor speed and desired motor current in a polynomial flow estimation algorithm to determine flow through the PAP device. The estimation algorithm in the preferred embodiment of the invention uses a two-dimensional look-up table, where the inputs are the desired current and actual motor speed, and the output is the flow through the PAP device. In a second, related embodiment, the current input in the table look-up operation is the actual motor current minus a component due to acceleration or deceleration, the current in this case being that 'desired' to maintain the motor speed.

BRIEF DESCRIPTION OF THE FIGURES

To further satisfy the recited objectives, a detailed description of typical embodiments of the invention is provided with reference to appended drawings that are not intended to limit the scope of the invention, in which.

DESCRIPTION OF THE INVENTION

Figure 2:
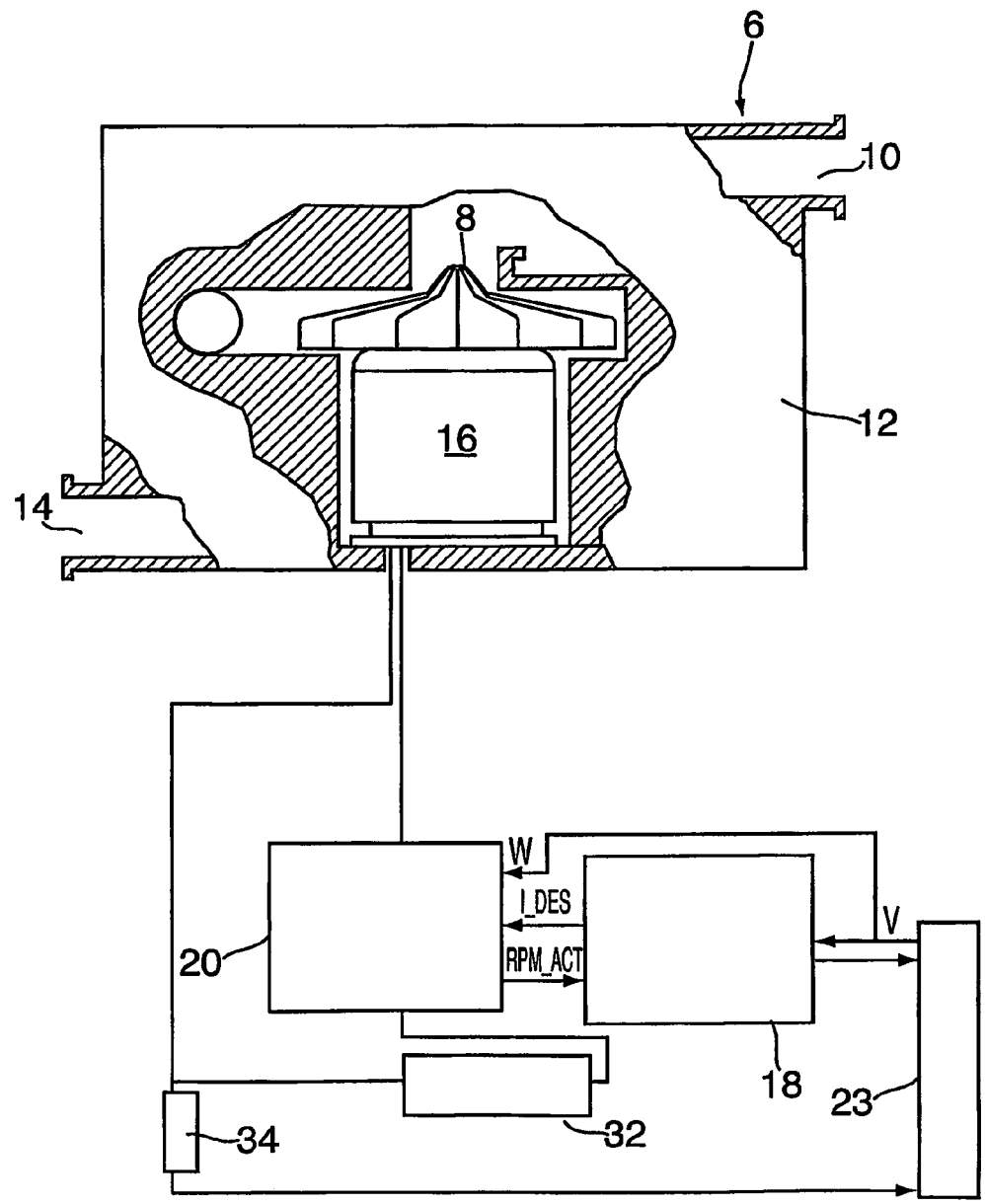
FIG. 2 is a schematic depiction of a PAP device according to the invention.

In FIG. 2, a system is disclosed for calculating flow. A blower 6 has a fan 8 which takes air from an inlet 10, applies torque to pressurize the air in a volute 12, and delivers the air through an outlet 14. During typical operation, the fan 8 rotates at approximately 20,000 RPM. Pressures delivered are capable of ranging from 4 to 20 cmH$_2$O with volumetric flows between 0 and 150 L/min. The illustrated blower 6 may be replaced by another blower/volute design, such as an axial fan, as long as the operating range encompasses these parameters.

A typical motor 16 powers the fan, where the motor is a 24V wound brushless DC motor. Other electric motors will respond in a similarly useful manner.

The system blower 6 is capable of imparting to the air a pressure head within the fan volute 12. A torque supplied by the motor causes work to be done on the air as it passes through the blower. In theory, the torque generated is related to the density of the air, the volumetric flow, the inner and outer radii of the impellers of the fan, and the tangential component of air flow velocity as it enters and leaves the blower. This relationship is given by:

$\tau = \rho Q (r_o V_o - r_i V_i)$, where $\tau$ = torque
$\rho$ = density
Q = volumetric flow
r = radius, and
V = tahgential air flow $\tau = KI$, where $\tau$ = torque
K = motor constant, and
I = winding current The total torque developed by the motor 16 is primarily used in three areas: maintaining speed against friction and viscous effects; changing the speed; and providing a pressure head and flow via the blower. Speed means the rotational velocity of the motor rotor and blower assembly. The torque developed by the motor 16 can ideally be related to current I flowing through the motor windings as proportional to the motor constant K, as in:

From these relationships it is possible to relate the current I in the motor windings to the volumetric flow Q through the blower 6 if the speed of the fan 8 is known.

The motor 16, fan 8, and pneumatic arrangement of the blower 6, air delivery tube and mask (not shown) can be mathematically modeled as a first order system where the energy required by the motor 16 is proportional to the mass of air delivered (where air is regarded as incompressible at the pressures involved). The transfer function derived from the first order equation is G=1/(as+k), where the energy loss component is due to the electronic and pneumatic losses in the system, including air re-circulation within the fan chamber, and air loss through leaks and the $CO_2$ flush. The damping component (further reducing energy delivered to the air) is due to the energy delivery mechanism involved with the compression, temperature increase, and pumping of air.

Artifacts excluded from these relationships include, for example, copper losses in the motor; turbulence developed within the volute; flow separation due to compression at the impeller tips; compressibility of the air; friction between the air and blower; variations in air density due to changes in altitude or temperature; variations in motor parameter K due to operating temperature; and variations in motor friction due to bearing grease changes, etc. The artifacts can be considered negligible in most systems but may lower the accuracy of the flow data and so should be considered in the light of poor system performance. The most significant artifact is the variation of air density. However, this can be overcome by relating current to mass flow instead of volumetric flow. This should be considered if the device is to operate at different altitudes.

The above equations describe an ideal situation for measuring Q. However, the actual model is very complex and difficult to model precisely. To overcome this problem, the system is empirically modeled, as described below, based on a physical understanding of the actual dynamics of the system.

The flow estimator algorithm of the present invention is a polynomial calculation that requires at least two inputs. The two input parameters are running parameters of the motor. A first input parameter to the flow estimator algorithm of the present invention is related to the motor speed. Preferably the input parameter is the actual motor speed, RPM_ACT. The actual motor speed, RPM_ACT, is determined preferably using one of the usual Hall-effect speed sensors in communication with the microcontroller. A second input parameter to the flow estimator algorithm is related to the motor current required to maintain the motor speed. This second input parameter is termed the desired motor current I_DES. There are a number of different ways in which the I_DES may be determined depending upon the control of the motor speed.

Referring to FIG. 2, the actual motor current, I_ACT, is measured using an amplifier and filter network 32 in the motor electronics. The motor current passes through a low inductance resistor 34 to ground. The voltage generated over this resistor is approximately proportional to the current passing through the motor windings: The actual motor current, I_ACT, is read by the microcontroller 18 using an analogue to digital converter. This method of measuring the I_ACT is, not specific to the operation of the flow estimation algorithm and other methods such as using Hall effect sensing are encompassed within the scope of the invention.

Figure 1:
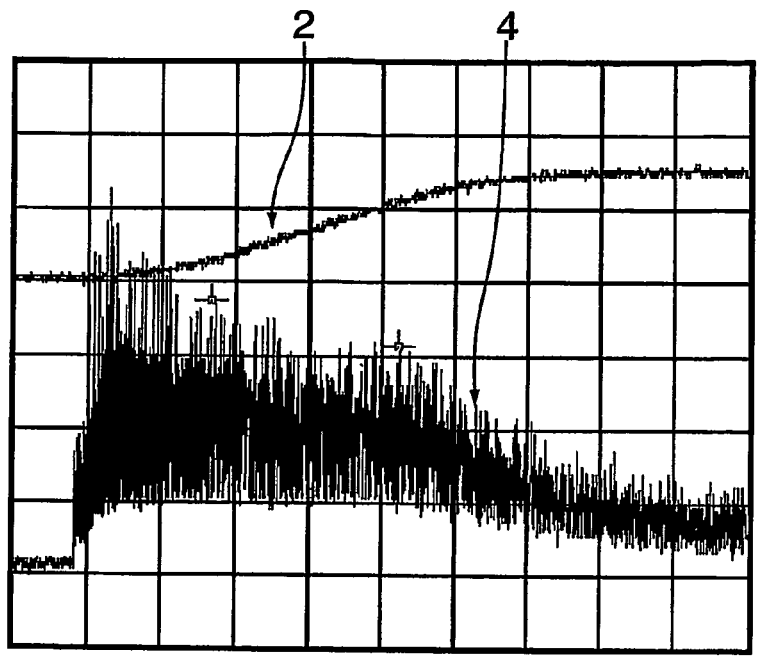
FIG. 1 is a trace of pressure versus actual motor current illustrating how noisy the motor winding current is in practice.
Figure 3:
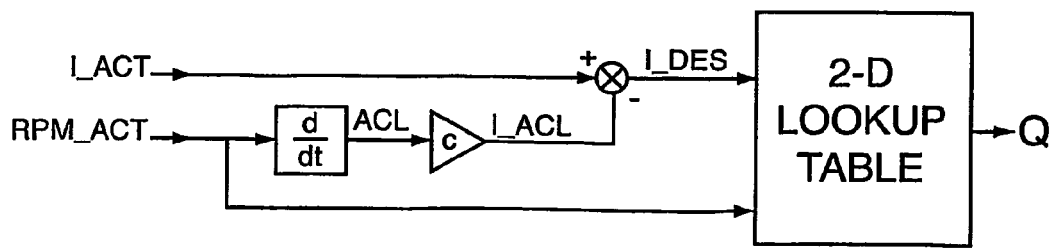
FIG. 3 illustrates the algorithmic process according a first embodiment of the invention.

In a first embodiment of the invention (see FIG. 3), the actual motor speed, RPM_ACT is measured and differentiated to provide an estimation of the rotor acceleration, ACL. The acceleration, ACL, is multiplied by a constant value C. The constant value C is preferably equal to the fan assembly inertia J divided by the motor constant K (C=J/K). The actual value of C is experimentally derived through calibration procedures to minimize the effects of unknown artifacts in the motor construction and miscalculation. The result is an estimation of the component of the overall current required for acceleration or deceleration of the motor, I_ACL (ACL× C=I_ACL).

In this embodiment the desired motor current I_DES is determined by subtracting the I_ACL from the measured actual motor current, I_ACT. The desired motor current, I_DES, is equivalent to the current used to maintain the motor speed and produce the airflow. The airflow is calculated using known operating parameters derived experimentally during a calibration process. The running parameters of the motor and fan characteristics are compressed into polynomial coefficients based on the known operating parameters of motor speed (RPM_ACT) and desired current (I_DES). Thus, the I_DES and RPM_ACT are fed through a polynomial calculation to determine the estimated airflow Q.

In a preferred embodiment the polynomial is calculated using an interpolating two-dimensional look-up table, where the inputs to the table are RPM_ACT and I_DES and the output is the airflow Q that existed at that operating point during calibration. Other structures and methods that relate RPM_ACT and I_DES to the airflow Q may be used in place of the look-up table.

Figure 4:
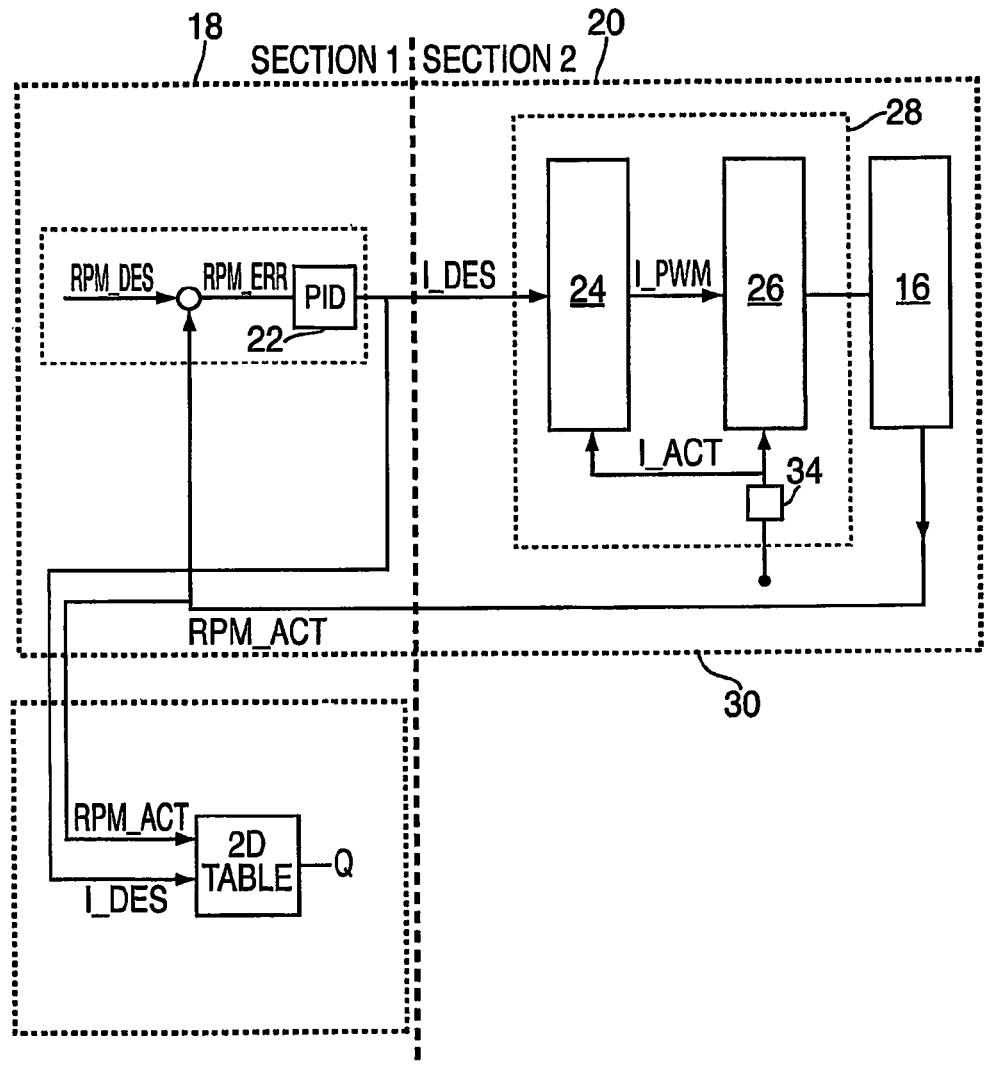
FIG. 4 illustrates an afternative preferred algorithmic process implemented by the device of FIG. 2.
Figure 5:
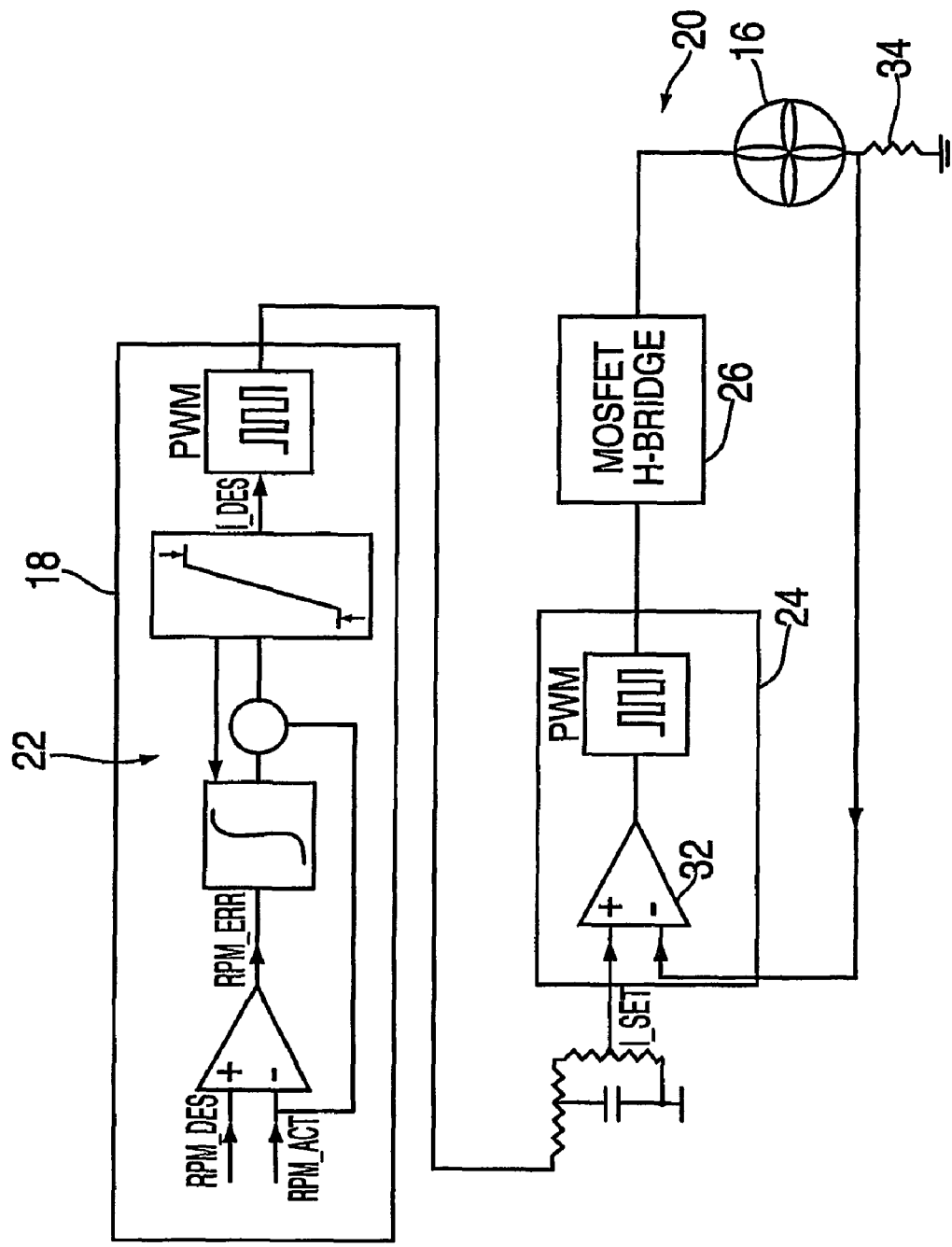
FIG. 5 illustrates the functions performed respectively by hardware and firmware in a preferred embodiment of the invention.

In a second preferred embodiment of the invention a control structure is present for maintaining the speed of the motor 16 (see FIGS. 2 and 4). It is to be appreciated that the speed is capable of changing because different speeds are required for different pressures. However, at a given fixed speed (or speed set point), the control structure of FIGS. 4 and 5 filters out perturbations from load or disturbance torque so that speed is essentially constant. Thus, there is minimal unintentional rotor acceleration such that acceleration is essentially equal to zero. Consequently there is no additional current due to acceleration, I_ACL, that needs to be considered in the flow estimation calculations. Thus, the actual current, I_ACT, may be considered substantially equivalent to the desired motor current I_DES.

In a most preferred embodiment of the invention the motor speed is maintained substantially constant using the motor control structure shown in FIG. 4 and the desired motor current, I_DES, input parameter is the determined motor current required to maintain the motor at the constant speed, wherein a servo controller maintains the actual motor current, I_ACT, close to the desired motor current, I_DES. This embodiment advantageously provides an additional advantage by using the clean servo input that controls the motor current, the desired motor current, I_DES, rather than the noisy measured actual motor current value, I_ACT.

The control structure (FIGS. 4 and 5) is a closed loop, two-stage speed controller, containing two sections 18 and 20 in a feedback loop. Section 1 resides in firmware on a Hitachi SH1 microcontroller that contains the flow estimation algorithm. A desired motor speed, RPM_DES, is specified by treatment algorithms native to the PAP device. The speed error, RPM_ERR, is calculated by subtracting the actual motor speed, RPM_ACT (determined as described above using one of the usual Hall-effect speed sensors in communication with the microcontroller), from the desired speed, RPM_DES. The desired set point comes from an internal lookup table, which converts a stored desired treatment pressure to the desired motor speed, RPM_DES. (The lookup table is valid at sea level but will be in error (underestimating the required motor speed) at higher altitudes.)

The actual motor speed RPM_ACT is subtracted from the desired speed RPM_DES (established by the required instantaneous pressure) to provide an error signal RPM_ERR that is fed to a tuned PID control system 22, and the output is a value corresponding to a desired motor current, I_DES. The integral forward term ensures zero static error, while the derivative feedback term permits optimal damping and stability without undue complexity. The specific PID implementation used is a pseudo-derivative feedback system, which avoids the actual calculation of a derivative term by injecting a proportional term after the integral in the forward path, as is known in the art. In a normal derivative feedback system with integral forward path, the derivative term is differenced with the set point to produce an error term containing derivative information. The error term is then integrated, producing a proportional forward term, whereby the same energy transfer function is provided as if the noise prone derivation was calculated. [See, "Automatic Control Systems" by Richard M. Phelan, Cornell University Press, 1987.]

In systems using integral forward terms, stability and transient recovery of large signals is obtained by limiting the integrator during non-linear behavior, such as during startup. Limiting the integrated output ensures that the final control output is within its linear range.

The desired signal, I_DES, varies as a change in torque is required by the motor to maintain a constant speed. The desired current, I_DES, provides a signal proportional to motor power, has stable and linear transfer function mappings and permits optimal usage of the capacity of the power supply 23 (FIG. 2). The more conventional usage of motor voltage as the final control variable (or using the actual motor current) has a grossly unstable and non-linear transfer function (as compared to the transfer function of the system) and requires additional current limiting protection for proper co-ordination between the energy supplied by the motor and the mass of air delivered to the patient.

Section 2 is implemented in hardware in the form of a MC33033 brushless DC motor control IC 24 with motor drive MOSFETs 26 in a feedback configuration with the microcontroller 18 (FIG. 4). An inner loop 28 of the control system, as part of the hardware 20, is in a feedback relationship with and accepts the desired motor current value, I_DES, from the outer loop 30 (which includes Section 1 and the blower). The power to the motor 16 is controlled via a pulse width modulated signal, I_PWM, that drives the power MOSFETs 26.

More specifically, the signal resulting from the software control loop is extended from the microcontroller 18 to the PWM control circuit 24. The input to the control circuit, I_DES, is low pass filtered and scaled down, providing I_SET, or the set point for the current that provides the correct motor speed, which is processed by the motor control hardware 20 to control the motor current. The motor control hardware is configured as a transconductance amplifier, so that the signal from the microcontroller can be treated as a current set point, I_SET, and converted into motor drive current.

The I_SET signal is fed to the positive input of the amplifier 32 (FIG. 5) and is used as the reference input. The actual motor current, I_ACT, is sensed via a voltage drop along a low inductance resistor 34 in series with the lower MOSFETs 26. This sensed motor current, I_ACT, is fed to the negative input of the amplifier 32 as a feedback signal. The amplifier 32 maintains the inner loop by acting as a comparator, shutting down the motor drive in each PWM cycle when the actual current; I_ACT, reaches the current set point I_SET. The controller therefore controls the peak motor drive current in each PWM cycle.

In all, there are six MOSFETs (i.e, a MOSFET H-bridge) driving the motor. Three of the MOSFETs are for the commutated upper legs of each phase, and three are for the lower leg of each phase.

In this preferred embodiment the flow rate estimation is based on a two-dimensional look-up table, where the inputs are the desired current, I_DES, and actual speed RPM_ACT, and the output is the flow Q. The values of the two dimensional table represent motor and fan characteristics compressed into polynomial coefficients based on the known operating parameters of motor speed, RPM_ACT, and desired motor current, I_DES. Accordingly, the interpolation process is equivalent to feeding I_DES and RPM through exact polynomial equations for determining the air flow Q.

The values of flow Q computed from speed RPM_ACT and desired current I_DES are those that existed at that operating point during calibration, where the experimentally derived values minimized error due to artifact. Here, the desired speed I_DES is representative of the actual winding current, I_ACT, but is not subject to signal noise as with the actual current. Accordingly, measuring flow with the less accurate value of the actual winding current, I_ACT, is not required. The feedback configuration allows the described desired current to be used instead.

In use, the patient breathes during the night, supported by the PAP device, and the airflow fluctuations through the blower assembly 6 change the torque required by the fan 8. This change in torque results in a change in current supplied to the motor 16 from the power supply 23, where the motor current is maintained by the control system of FIGS. 4 and 5. The value of the desired motor current (I_DES) can then be determined by monitoring the control system and the motor current is adjusted by the control system in order to maintain rotor speed. The motor speed is measured using Hall-effect sensors (built into the motor stator) in commutation between the motor and the motor controller 20 so that the motor speed (RPM_ACT) may be reported back to the microcontroller 18.

The algorithmic process holds the motor speed (RPM_ACT) to an acceptably constant value using the motor controller hardware 28 and microcontroller 18, resulting in minimal unintentional rotor acceleration values. The actual motor current I_ACT is equivalent to the desired current I_DES used to maintain motor speed against friction and produce the airflow (except for the nonlinear effects in the actual current, discussed above). Finally, the value of the desired current I_DES and the actual speed of the blower RPM_ACT are fed to the flow estimator algorithm which provides the flow at that instant.

Other structures and methods that relate RPM_ACT and I_DES to the airflow Q are just as valid and could easily be implemented in place of the look-up table method without detracting from the operation of the flow estimator as a whole. Furthermore, the flow estimation algorithms are performed on the same microcontroller (Hitachi SH1) as the motor control and treatment algorithms. However, any logic device could conceivably be used to estimate the flow and it may be a device separate from other control devices. The requirements placed upon the devices used by the flow estimation are the processing speed and memory required by the algorithms. Therefore, a different microcontroller or logic structure could be employed without affecting the flow estimation. Furthermore) other values that are internal to the controller and proportional to flow Q may be substituted for I_DES to determine flow 0, such as the integral term of the PID.

The structure of the control system is arbitrary and the requirements are that a desired motor current is present in the software part of the control structure and is accessible to the flow estimation algorithms. The control structure that regulates the winding current is capable of regulating the motor current to sufficiently small error tolerances to allow assumptions of the motor current to be valid. Additionally, the control system as a whole performs sufficiently well to maintain motor speed to small enough error tolerances that make assumptions of the speed performance acceptable, and does not degrade flow estimation performance beyond unacceptable levels.

Accordingly, a method and apparatus have been disclosed for determining airflow through a PAP device while applying PAP therapy. The method comprises the steps of determining the actual speed of a blower motor and comparing it to a desired speed, determining the desired motor current so that the motor speed approaches the desired speed, and using the actual blower motor speed and desired motor current in a flow estimation algorithm to determine flow through the PAP device. The estimation algorithm uses a two-dimensional look-up table, where the inputs are the desired current and actual motor speed, and the output is the flow through the PAP device.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

What is claimed is:

1. A method for determining airflow through a PAP device while applying PAP therapy comprising the steps of:
   measuring, using a sensor, the actual speed of a blower motor;
   determining, using a controller, a desired motor current so that the motor speed approaches a desired speed, the desired current determined by deriving an acceleration current by differentiating the actual motor speed and subtracting the acceleration current from an actual motor current; and
   using, through the controller, the actual motor speed and desired motor current in a flow estimation algorithm to determine flow through the PAP device.

2. The method of claim 1 wherein the estimation algorithm uses a two-dimensional look-up table, where the inputs are the desired current and actual motor speed, and the output is the flow through the PAP device.

3. The method of claim 1 wherein the actual motor current is used in a servo loop with the desired current to control the motor speed.

4. An apparatus for determining airflow through a PAP device while applying PAP therapy wherein the apparatus comprises:
   a sensor that measures the actual speed of a blower motor;
   a controller that determines a desired motor current so that the motor speed approaches a desired speed, the desired current determined by deriving an acceleration current by differentiating the actual motor speed and subtracting the acceleration current from an actual motor current; and
   the controller uses the actual motor speed and desired motor current in a flow estimation algorithm to determine flow through the PAP device.

5. The apparatus of claim 4 wherein the estimation algorithm uses a two-dimensional look-up table, where the inputs are the desired current and actual motor speed, and the output is the flow through the PAP device.

6. The apparatus of claim 4 wherein the actual motor current is used with the desired current to control the motor speed.

7. A method for determining airflow through a PAP device while applying PAP therapy comprising the steps of:
measuring using a sensor the actual speed of a blower motor;
determining using a controller a desired motor current required to maintain a desired motor speed by deriving an acceleration current component is derived by differentiating the actual motor speed, and the desired motor current is determined by subtracting the acceleration current component from an actual motor current; and
using through the controller both the actual motor speed and desired motor current in a polynomial flow estimation algorithm to determine flow through the PAP device.

8. The method of claim 7 wherein the desired motor speed is equal to the measured actual motor speed.

9. The method of claim 8 further comprising measuring the actual motor current.

10. The method of claim 7 wherein the actual motor current is measured and used in a servo loop with the resulting desired motor current to control the motor speed.

11. The method of claim 7 wherein the estimation algorithm uses a two-dimensional look-up table, where the inputs are the desired motor current and actual motor speed, and the output is the flow through the PAP device.

12. An apparatus for determining airflow through a PAP device while applying PAP therapy wherein the apparatus comprises:
a sensor that measures the actual speed of a blower motor;
a controller that determines a desired motor current required to maintain a desired motor speed, the desired current determined by deriving an acceleration current by differentiating the actual motor speed and subtracting the acceleration current from an actual motor current; and
the controller using both the actual motor speed and desired motor current in a polynomial flow estimation algorithm to determine flow through the PAP device.

13. A method for determining airflow through a PAP device while applying PAP therapy comprising the steps of:
generating, using a sensor, a speed dimension parameter based on an actual speed of a blower motor;
measuring an actual motor current of the blower motor;
deriving an acceleration current component by differentiating the actual motor speed;
generating, using a processor, a current dimension parameter by subtracting the acceleration current component from the actual motor current;
determining, using the processor, flow through the PAP device using the speed-dimension parameter and the current-dimension parameter in a flow estimation algorithm.

14. The method of claim 13 wherein the flow estimation algorithm uses a two-dimensional look-up table, where the inputs are the speed—dimension parameter and the current—dimension parameter, and the output is the flow through the PAP device.

15. The method of claim 13 wherein the actual motor current is used in a servo loop with the current dimension parameter to control the motor speed.

* * * * *